United States Patent
Sizer

(10) Patent No.: US 7,481,974 B2
(45) Date of Patent: *Jan. 27, 2009

(54) METHOD AND APPARATUS FOR STERILIZING CONTAINERS

(75) Inventor: Charles E. Sizer, Naperville, IL (US)

(73) Assignee: Charles Sizer, Naperville, IL (US)

( * ) Notice: Subject to any disclaimer, the term of this patent is extended or adjusted under 35 U.S.C. 154(b) by 722 days.

This patent is subject to a terminal disclaimer.

(21) Appl. No.: 11/060,459

(22) Filed: Feb. 17, 2005

(65) Prior Publication Data

US 2006/0182653 A1    Aug. 17, 2006

(51) Int. Cl.
*A61L 2/00* (2006.01)
*A61L 9/00* (2006.01)

(52) U.S. Cl. .................. 422/28; 422/29; 422/304

(58) Field of Classification Search .............. 422/28, 422/29; 53/426
See application file for complete search history.

(56) References Cited

U.S. PATENT DOCUMENTS

| | | | |
|---|---|---|---|
| 3,899,862 A | | 8/1975 | Muys et al. |
| 5,326,542 A | | 7/1994 | Sizer et al. |
| 5,328,706 A | | 7/1994 | Endico |
| 5,344,652 A | | 9/1994 | Hall, II et al. |
| 5,470,930 A | * | 11/1995 | Toba et al. ............ 526/204 |
| 5,540,885 A | * | 7/1996 | Pahlmark et al. ......... 422/28 |
| 5,578,134 A | | 11/1996 | Lentsch et al. |
| 5,770,232 A | | 6/1998 | Sizer et al. |
| 5,843,374 A | | 12/1998 | Sizer et al. |
| 5,876,812 A | | 3/1999 | Frisk et al. |
| 5,900,111 A | | 5/1999 | Nystrom et al. |
| 5,928,607 A | | 7/1999 | Frisk |
| 6,094,887 A | | 8/2000 | Swank et al. |
| 6,209,591 B1 | | 4/2001 | Taggart |
| 6,458,240 B1 | | 10/2002 | Bouchette et al. |
| 6,479,454 B1 | | 11/2002 | Smith et al. |
| 6,481,468 B1 | | 11/2002 | Taggart |
| 6,536,188 B1 | | 3/2003 | Taggart |
| 6,537,492 B1 | | 3/2003 | Sogaard |
| 2002/0083682 A1 | | 7/2002 | Edwards et al. |
| 2002/0085971 A1 | | 7/2002 | Raniwala |
| 2007/0006551 A1 | * | 1/2007 | Sizer ..................... 53/426 |

FOREIGN PATENT DOCUMENTS

| | | |
|---|---|---|
| EP | 0411970 | 2/1991 |
| JP | 07-291236 | 11/1995 |

OTHER PUBLICATIONS

Search Report for PCT Application Number PCT/US2006/004840.
International Preliminary Examination Report for PCT/US2006/004840.

* cited by examiner

*Primary Examiner*—Jill Warden
*Assistant Examiner*—Kevin C Joyner
(74) *Attorney, Agent, or Firm*—Clause Eight LLP; Michael Catania

(57) ABSTRACT

A method (20) and apparatus (100) for sterilizing packaging (102) is disclosed herein. The method (20) applies a solution of hydrogen peroxide onto the packaging (102) and an alkaline solution to react with the hydrogen peroxide to generate hydroxyl radicals to kill microorganism. The use of an alkaline solution allows the sterilization process to proceed at a lower temperature and a faster rate. A solution of sodium hydroxide is the preferred alkaline solution. The temperature of the process is preferably below 100° C.

16 Claims, 5 Drawing Sheets

METHOD AND APPARATUS FOR STERILIZING CONTAINERS

CROSS REFERENCES TO RELATED APPLICATION

Not Applicable

STATEMENT REGARDING FEDERALLY SPONSORED RESEARCH OR DEVELOPMENT

Not Applicable

BACKGROUND OF THE INVENTION

1. Field of the Invention

The present invention is related to a method and apparatus for sterilizing or disinfecting containers. More specifically, the present invention relates to a method and apparatus for sterilizing containers at relatively low temperatures.

2. Description of the Related Art

Sterilization of food and medicinal packaging is necessary to kill microorganisms that may be present on the packaging. The failure to properly sterilize food packaging could lead to contamination of the food within the packaging, which could lead to sickness and sometimes death to a consumer of the food. The food industry has developed various methods to sterilize food packaging to create aseptic packaging.

Traditional aseptic packaging is typically sterilized using hydrogen peroxide. As set forth in Title 37 of the Code of Federal Regulations ("CFR"), Section 178.1005, the U.S. Food and Drug Administration ("FDA") has determined that a hydrogen peroxide solution containing not more than 35% hydrogen peroxide may be safely used to sterilize polymeric food-contact surfaces. Sterilization using hydrogen peroxide typically requires high temperatures or ultraviolet light to generate hydroxyl radicals from the hydrogen peroxide, which in turn inactivate the microorganisms on the packaging material. The temperature needed to generate free radicals from the hydrogen peroxide is usually in excess of 65° C. and is frequently in the range of 120-135° C.

Most food packaging is composed of a polymer material such as plastic bottles. The FDA has provided a list of polymer materials that may be utilized with hydrogen peroxide. The list, set forth in 37 CFR 178.1005(e), includes ethylene-acrylic acid copolymers, ethylene-carbon monoxide copolymers, ethylene-methyl acrylate copolymer resins, ethylene-vinyl acetate copolymers, ionomeric resins, isobutylene polymers, olefin polymers, polycarbonate resins, polyethylene terephthalate ("PET"), poly-1-butene resins and butane/ethylene copolymers, polystyrene and rubber modified polystyrene polymers and vinylidene chloride/methyl acrylate copolymers. Sterilization of plastic bottles is difficult at elevated temperatures since the bottles become quite fluid and deform during the sterilization process. In addition, an extended drying process is required to evaporate the residue of peroxide (35%) which boils at 108° C. Further, some plastic materials like PET bind or absorb peroxide making it very difficult to achieve the residue limit of 0.5 parts per million ("ppm") for food packaging required by the FDA as set forth in 37 CFR 178.1005(d).

One method of sterilization is disclosed in Sizer et al., U.S. Pat. No. 5,326,542 for a Method And Apparatus For Sterilizing Cartons, which discloses using ultraviolet light to sterilize food cartons.

Another method is disclosed in Sizer et al., U.S. Pat. No. 5,770,232 for a Method Of Disinfecting The Food Contact Surfaces Of Food Packaging Machines And Disinfecting Solution Therefor, which discloses using a solution of 0.1% to about 1% by weight of hydrogen peroxide and from about 0.001% to about 0.1% by weight of sodium acid pyrophosphate applied at a temperature of about 70° C. for at least fifteen minutes.

Another method is disclosed in Frisk, U.S. Pat. No. 5,928,607 for a Bottle Sterilization Method And Apparatus, which discloses using ultraviolet radiation from an excimer lamp to generate ozone from oxygen to sterilize plastic bottles.

Another method is disclosed in Lentsch et al., New Zealand Patent Number 282691 for a Method For Sanitizing And Destaining Food Ware And Utensils Using A Composition Comprising Peroxycarboxylic Acid, Carboxylic Acid, Peroxide And A Carrier, discloses a sanitizing concentrate composition of 1-20 weight % peroxycarboxylic acid, 10-50 weight % carboxylic acid, 3-35 weight % hydrogen peroxide and the balance a carrier.

Yet another method is disclosed in Wang, European Patent Number 0411970 for Sterilization Of Containers By Means Of Hydrogen Peroxide, Peracids, And U.V. Radiation, which discloses using between 15 to 25% concentration of hydrogen peroxide and peracetic acid at a temperature of 20-30° C. with U.V. light at a wavelength of less than 300 nanometers for 8-12 seconds to effectuate a greater than 6.0 log reduction in the number of $B.\ subtilis$ spores.

Yet another method is disclosed in Smith et al., U.S. Pat. No. 6,479,454 for Antimicrobial Compositions And Method Containing Hydrogen Peroxide And Octyl Amine Oxide, which discloses using a composition of an amine oxide hydrogen peroxide to sanitize food contact surfaces.

Another method is disclosed in Taggart, U.S. Pat. No. 6,209,591 for an Apparatus And Method For Providing Container Filling In An Aseptic Processing Apparatus, which discloses spraying atomized hydrogen peroxide onto bottles within a sterilization chamber that has sterile air present at a temperature of 135° C.

Another method is disclosed in Taggart, U.S. Pat. No. 6,536,188 for a Method And Apparatus For Aseptic Packaging, which discloses spraying hot hydrogen peroxide onto bottles, allowing approximately 24 seconds for activation and removal of the hydrogen peroxide, and then filling the bottle with a low acid beverage.

Hall, II et al., U.S. Pat. No. 5,344,652 for a Anticorrosive Microbicide discloses a two part component containing a first part of hydrogen peroxide, peracetic acid and acetic acid, and a second part of VICTAWET®, which is a sodium hydroxide reaction product of an aliphatic alcohol (2-ethyl hexyl) and phosphorous pentoxide. The VICTAWET® reduces the corrosiveness of the peroxide/peracetic biocide.

Nystrom et al., U.S. Pat. No. 5,900,111 for a Process For Sanitizing Post-Consumer Paper Fibers Using Heat And Hydrogen Peroxide discloses sanitizing waste paper hydrogen peroxide and using sodium hydroxide to adjust the pH of a fiber stream during the sanitizing process.

Japanese Patent Publication Number 02-154763 for a Method For Removing Hydrogen Peroxide discloses removing excess hydrogen peroxide from soft contact lenses subjected to a hydrogen peroxide sterilization treatment by using a removing agent essentially consisting of sodium thiosulfate, sodium pyruvate, peroxidase and a metallic catalyst, with the soft contact lenses also subjected to ultrasonic waves.

Japanese Patent Publication Number 07-291236 for a Method Of Sterilizing Food Container discloses using hot water with a germicide forced into an interior of a food container, with the germicide being hydrogen peroxide, peracetic acid, mixture of hydrogen peroxide and peracetic acid or sodium hypochlorite.

Although the prior art has disclosed many different methods for sterilizing containers, especially food containers, there is still a need for using hydrogen peroxide at low temperatures in an expedited manner in order to reduce costs, increase container filling productivity and most importantly adequately sterilize the containers.

BRIEF SUMMARY OF THE INVENTION

The present invention provides a solution to the need for a low temperature sterilization process. The present invention is able to accomplish this by using a two component solution of hydrogen peroxide and an alkaline solution. The alkaline solution quickly reacts with hydrogen peroxide to generate active oxygen species including hydroxyl radicals to destroy microorganisms.

One aspect of the present invention is a method for sterilizing packaging. The method begins by applying a hydrogen peroxide solution having from 1% to 50% hydrogen peroxide to packaging. The hydrogen peroxide solution is applied at a temperature ranging from 35° C. to 100° C. Next, the hydrogen peroxide solution is permitted to activate on the packaging for an activation period of at least about one second. Next, an alkaline solution is applied to the packaging subsequent to the activation period. The alkaline solution has a pH in the range of 10-14. The alkaline solution is applied at a temperature ranging from 35° C. to 100° C. Next, the packaging is rinsed with sterile water to remove the residue alkaline solution and residue hydrogen peroxide.

Another aspect of the present invention is a method for sterilizing a plastic bottle. The method beings with applying a hydrogen peroxide solution having from 30% to 40% hydrogen peroxide to an exterior surface of the plastic bottle and an interior surface of the plastic bottle. The hydrogen peroxide solution is applied at a temperature ranging from 40° C. to 60° C. Next, the hydrogen peroxide solution is permitted to activate on the exterior surface of the plastic bottle and the interior surface of the plastic bottle for an activation period ranging from 1 second to 10 seconds. Next, a solution of 0.25 Normal sodium hydroxide is applied to the exterior surface of the plastic bottle and the interior surface of the plastic bottle subsequent to the activation period. The solution of 0.25 Normal sodium hydroxide has a pH in the range of 11-13. The solution of 0.25 Normal sodium hydroxide is applied at a temperature ranging from 50° C. to 75° C. Next, the packaging is rinsed with sterile water to remove the residue sodium hydroxide and residue hydrogen peroxide.

Yet another aspect of the present invention is a method for sterilizing packaging at a low temperature. The method begins by applying a hydrogen peroxide solution having from 1% to 50% hydrogen peroxide to packaging. The hydrogen peroxide solution is applied at a temperature no greater than 65° C. Next, the hydrogen peroxide solution is permitted to activate on the packaging for an activation period ranging from 1 second to 30 seconds. Next, an alkaline solution is applied to the packaging subsequent to the activation period. The alkaline solution has a pH in the range of 10-14. The alkaline solution is applied at a temperature no greater than 65° C. Next, the packaging is rinsed with sterile water to remove the residue alkaline solution and residue hydrogen peroxide.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
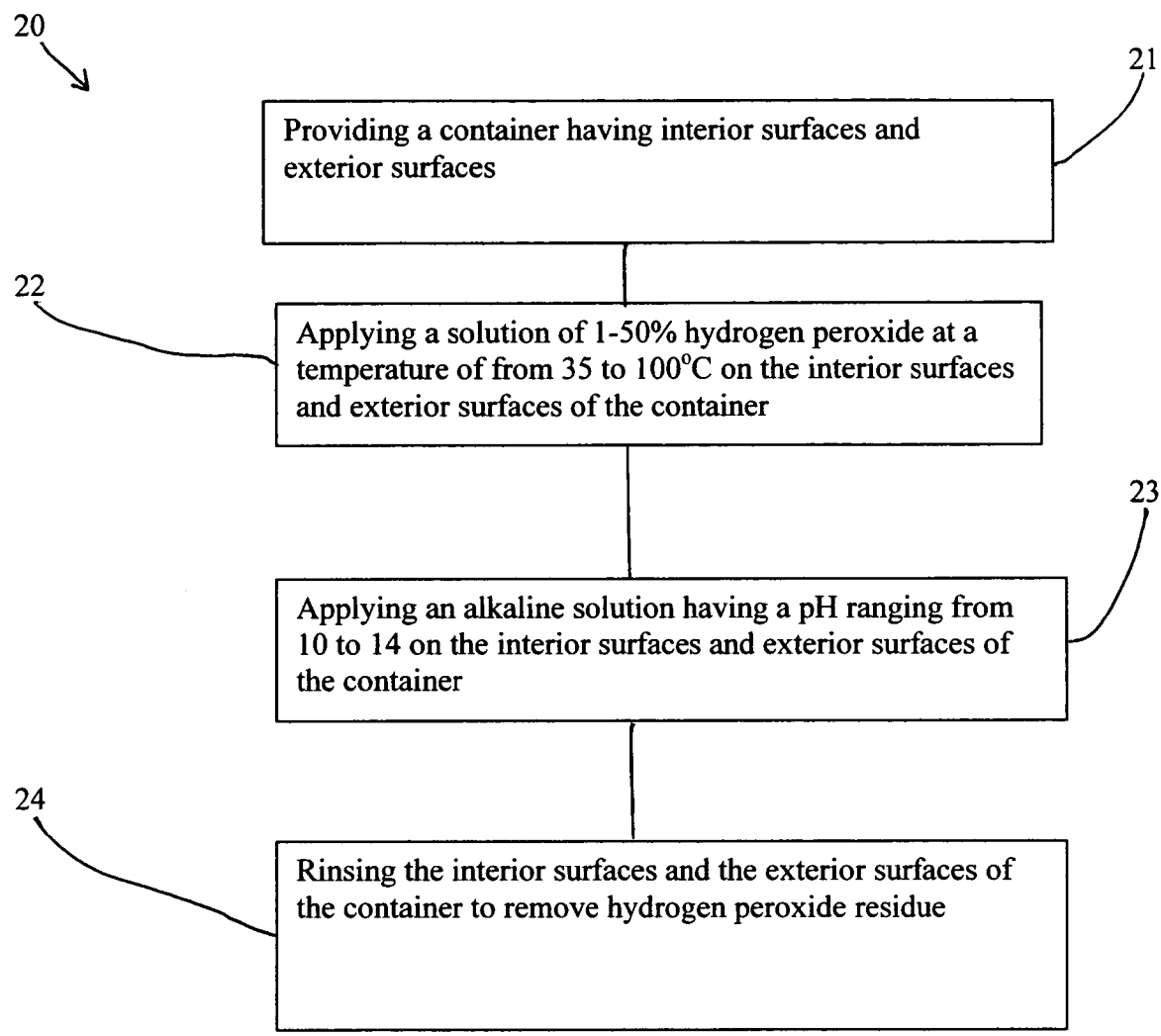
FIG. 1 is a flow chart of a general method of the present invention.

As illustrated in FIG. 1, a general method of sterilizing containers, especially food containers, is designated 20. At block 21, a container is provided for sterilization. The container has interior surfaces and exterior surfaces, with both surfaces preferably requiring sterilization. The container is preferably a food container, although other types of containers requiring sterilization such as containers for eye-care products, medical products and the like are within the scope and spirit of the present invention. Preferably the container is composed of a polymer material or glass, although containers composed of other materials are within the scope and spirit of the present invention. A preferred polymer material is PET or high density polyethylene.

At block 22, a solution of 1% to 50% hydrogen peroxide is applied to the interior surfaces and the exterior surfaces of the container. The hydrogen peroxide solution is preferably applied at a temperature ranging from 35° C. to 100° C., more preferably at a temperature ranging from 35° C. to 85° C., even more preferably at a temperature ranging from 40° C. to 60° C., and most preferably at a temperature of 50° C. The solution of hydrogen peroxide preferably has a concentration ranging from 1% to 50% hydrogen peroxide, more preferably 30% to 40%, and most preferably 35%. The hydrogen peroxide is preferably applied to the container in a liquid form. Alternatively, the hydrogen peroxide is applied as a vapor and allowed to condense on the surfaces of the container. The solution of hydrogen peroxide is preferably allowed to remain on the surfaces of the container for an activation time period of 30 seconds, more preferably less than 30 seconds, even more preferably less than 10 seconds, and most preferably one second or less.

After the activation time period, an alkaline solution is applied to the surfaces of the container as set forth in block 23. The alkaline solution preferably has a pH ranging from 10 to 14, more preferably from 11 to 13, and most preferably 12.5 or 12.9. The alkaline solution is preferably a sodium hydroxide solution or potassium hydroxide solution. However, those skilled in the pertinent art will recognize that other alkaline solutions may be utilized without departing from the scope and spirit of the present invention. The alkaline solution is preferably applied at a temperature ranging from 35° C. to 100° C., more preferably at a temperature ranging from 35° C. to 85° C., even more preferably at a temperature ranging from 50° C. to 75° C., and most preferably at a temperature of 65° C. The alkaline solution is preferably a 0.05 Normal solution of sodium hydroxide (approximately 0.20% concentration of sodium hydroxide). Alternatively, a one Normal solution of sodium hydroxide is utilized as the alkaline solution. In yet another alternative embodiment, a 0.1 Normal solution of potassium hydroxide is utilized as the alkaline solution. The alkaline solution reacts with the hydrogen peroxide to generate active oxygen species and hydroxyl radicals which kill the microorganisms on the surfaces of the container. The alkaline solution lessens the sterilization time to achieve aseptic conditions. Further, the alkaline solution decreases the absorption of hydrogen peroxide by the container and also hydrogen peroxide residue. Yet further, the alkaline solution allows the sterilization process to be performed at lower temperatures than the prior art sterilization methods, which allows for the use of thinner wall containers.

At block 24, the interior surfaces and exterior surfaces of the container are rinsed to remove hydrogen peroxide residue and also any alkaline solution. Preferably, the surfaces of the container are rinsed with sterile water, or alternatively an acid rinse such as citric acid or other similar acids. Subsequent to the rinsing, the containers are filled with a product. Preferably the containers are filled with a food product such as orange juice (high acid product), milk (low acid product), water, juices, soups or other similar foods.

Figure 2:
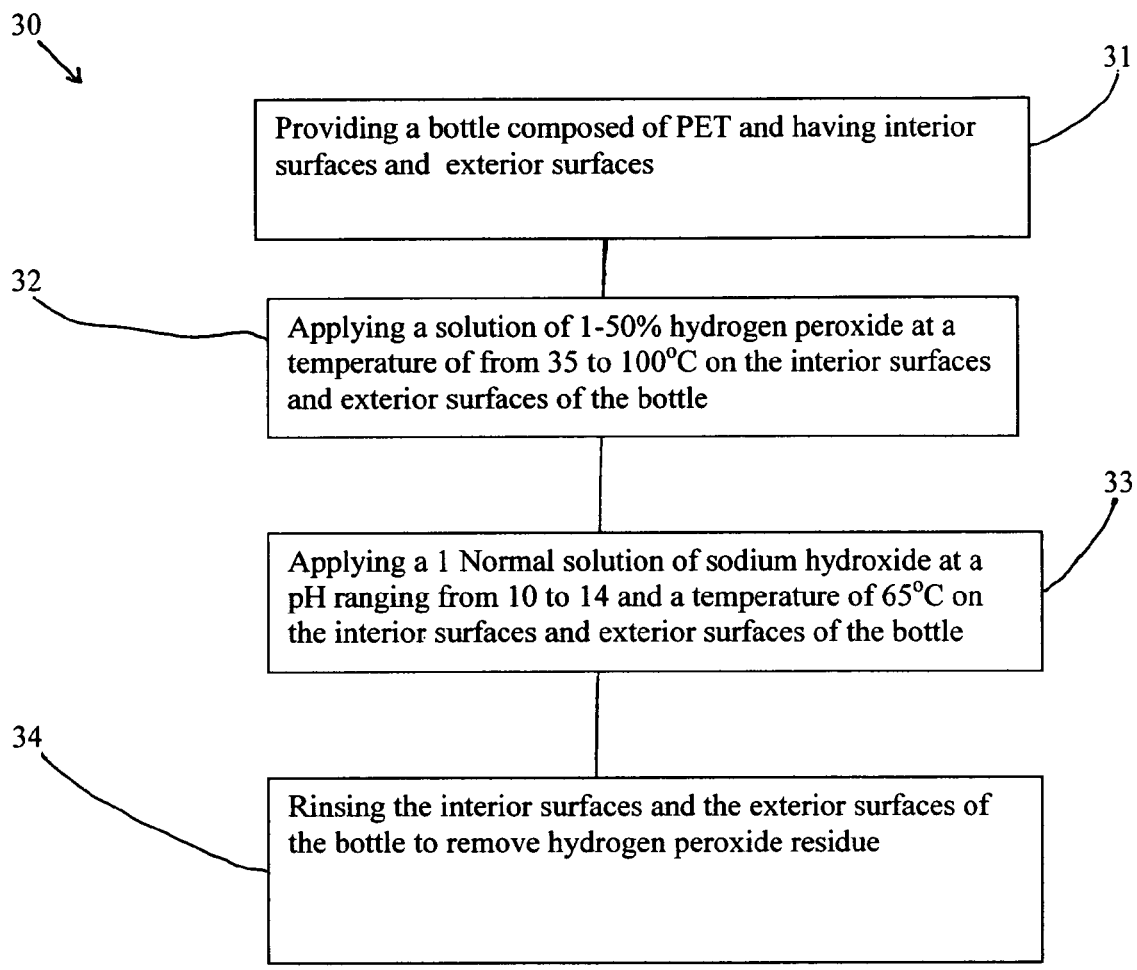
FIG. 2 is a flow chart of a specific method of the present invention.

A more specific sterilization method is illustrated in FIG. 2. The specific sterilization method is generally designated 30. At block 31, a bottle composed of PET or a PET derivative is provided for sterilization, generally on a filling machine. Most water bottles and orange juice containers are composed of PET or a PET derivative.

At block 32, a solution of 1% to 50% hydrogen peroxide is applied to the interior surfaces and the exterior surfaces of the container. The hydrogen peroxide solution is preferably applied at a temperature ranging from 35° C. to 100° C., more preferably at a temperature ranging from 35° C. to 85° C., even more preferably at a temperature ranging from 40° C. to 60° C., and most preferably at a temperature of 50° C. The solution of hydrogen peroxide preferably has a concentration ranging from 1% to 50% hydrogen peroxide, more preferably 30% to 40%, and most preferably 35%. The hydrogen peroxide is preferably applied to the container in a liquid form. Alternatively, the hydrogen peroxide is applied as a vapor and allowed to condense on the surfaces of the container. Although there is no upper limit, the solution of hydrogen peroxide is preferably allowed to remain on the surfaces of the container for an activation time period of 30 seconds, more preferably less than 30 seconds, even more preferably less than 10 seconds, and most preferably one second or less.

After the activation time period, a solution of sodium hydroxide is applied to the surfaces of the container as set forth in block 33. The sodium hydroxide solution preferably has a pH ranging from 10 to 14, more preferably from 11 to 13, and most preferably 12.5 or 12.9. The sodium hydroxide solution is preferably applied at a temperature of approximately 65° C. The sodium hydroxide solution is preferably a 0.05 Normal solution of sodium hydroxide (approximately 0.20% concentration of sodium hydroxide). Alternatively, a one Normal solution of sodium hydroxide is utilized as the alkaline solution. The sodium hydroxide solution reacts with the hydrogen peroxide to generate active oxygen species and/or hydroxyl radicals which kill the microorganisms on the surfaces of the container. The sodium hydroxide solution lessens the sterilization time to achieve aseptic conditions. Further, the sodium hydroxide solution decreases the absorption of hydrogen peroxide by the container and also hydrogen peroxide residue. Yet further, the sodium hydroxide solution allows the sterilization process to be performed at lower temperatures than the prior art sterilization methods, which allows for the use of thinner wall containers.

At block 34, the interior surfaces and exterior surfaces of the PET bottle are rinsed to remove hydrogen peroxide residue and also any sodium hydroxide solution. Preferably, the surfaces of the container are rinsed with sterile water. Subsequent to the rinsing, the containers are filled with a product. Preferably the containers are filled with a food product such as orange juice (high acid product), milk (low acid product), water, juices, soups or other similar foods.

Figure 3:
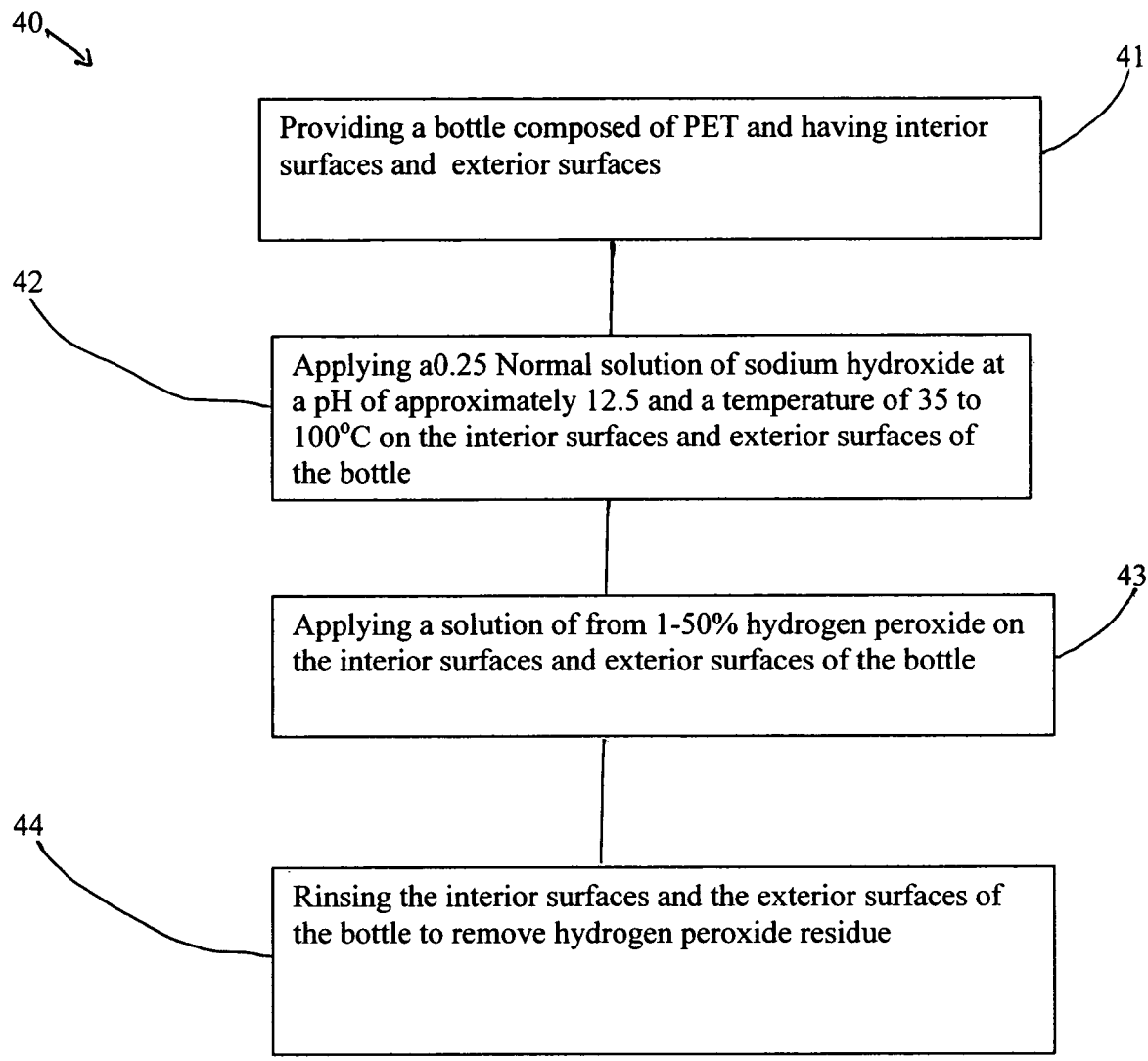
FIG. 3 is a flow chart of a specific method of the present invention.

An alternative method with a different sequence is illustrated in FIG. 3. The method is generally designated 40. At block 41, a bottle composed of PET or a PET derivative is provided for sterilization, generally on a filling machine. Most water bottles and orange juice containers are composed of PET or a PET derivative.

A solution of sodium hydroxide is first applied to the surfaces of the container as set forth in block 42. The sodium hydroxide solution preferably has a pH of approximately 12.5. The sodium hydroxide solution is preferably applied at a temperature ranging from 35° C. to 100° C., more preferably at a temperature ranging from 35° C. to 85° C., even more preferably at a temperature ranging from 50° C. to 75° C., and most preferably at a temperature of 65° C. The sodium hydroxide solution is preferably a 0.05 Mole solution of sodium hydroxide (approximately 0.20% concentration of sodium hydroxide). Alternatively, a one Normal solution of sodium hydroxide is utilized as the alkaline solution.

At block 43, a solution of 1% to 50% hydrogen peroxide is applied to the interior surfaces and the exterior surfaces of the container. The hydrogen peroxide solution is preferably applied at a temperature ranging from 35° C. to 100° C., more preferably at a temperature ranging from 35° C. to 85° C., even more preferably at a temperature ranging from 40° C. to 60° C., and most preferably at a temperature of 50° C. The solution of hydrogen peroxide preferably has a concentration ranging from 1% to 50% hydrogen peroxide, more preferably 30% to 40%, and most preferably 35%. The hydrogen peroxide is preferably applied to the container in a liquid form. Alternatively, the hydrogen peroxide is applied as a vapor. The sodium hydroxide solution reacts with the hydrogen peroxide to generate hydroxyl radicals which kill the microorganisms on the surfaces of the container. The sodium hydroxide solution lessens the sterilization time to achieve aseptic conditions. Further, the sodium hydroxide solution decreases the absorption of hydrogen peroxide by the container and also hydrogen peroxide residue. Yet further, the sodium hydroxide solution allows the sterilization process to be performed at lower temperatures than the prior art sterilization methods, which allows for the use of thinner wall containers.

At block 44, the interior surfaces and exterior surfaces of the PET bottle are rinsed to remove hydrogen peroxide residue and also any sodium hydroxide solution. Preferably, the surfaces of the container are rinsed with sterile water. Subsequent to the rinsing, the containers are filled with a product. Preferably the containers are filled with a food product such as orange juice (high acid product), milk (low acid product), water, juices, soups or other similar foods.

Figure 4:
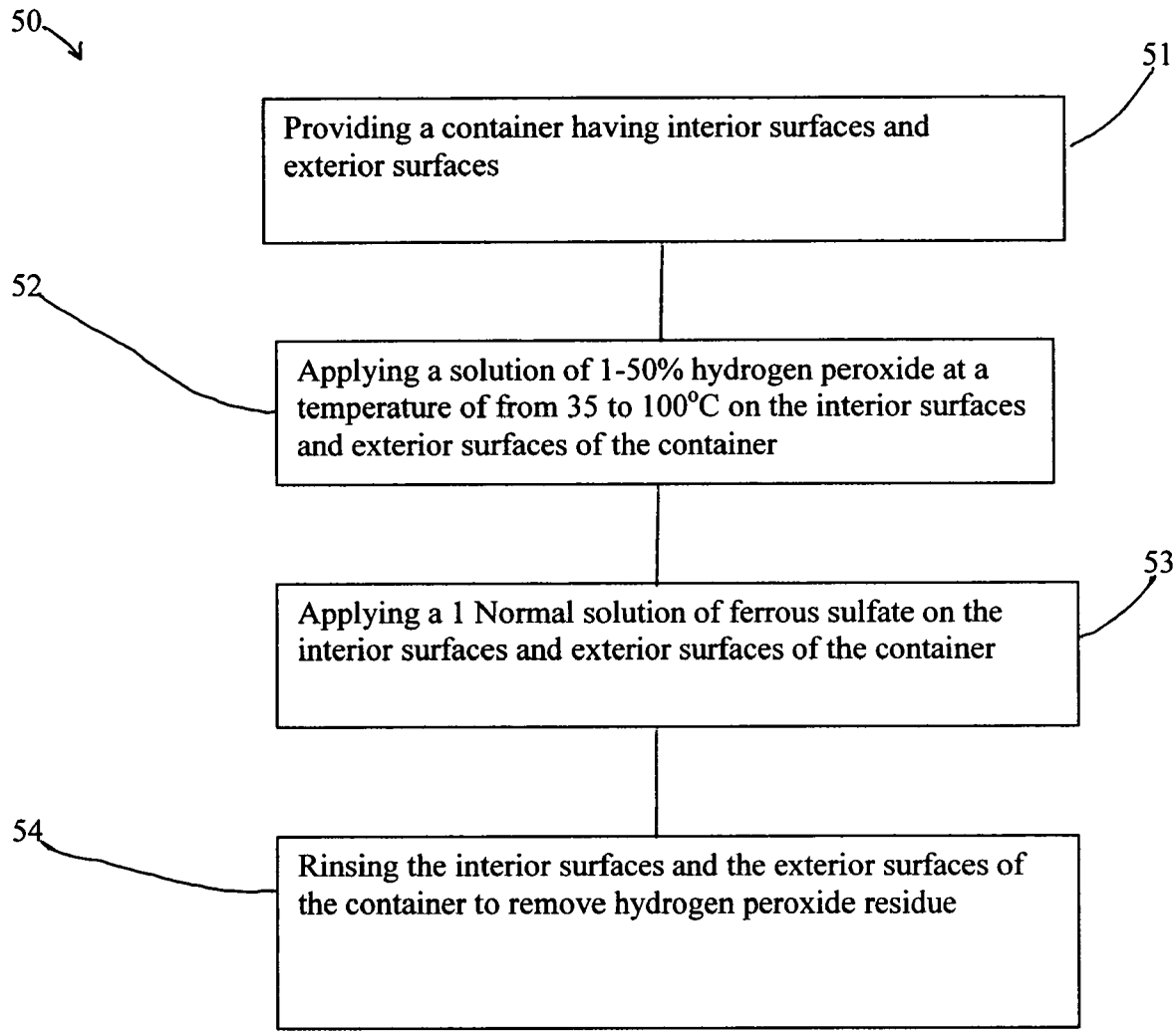
FIG. 4 is a flow chart of a specific method of the present invention.

An alternative sterilization method is illustrated in FIG. 4. The alternative sterilization method is generally designated 50. At block 51, a container is provided for sterilization, generally on a filling machine. The container is preferably composed of a polyethylene or polypropylene material. Most milk jugs are composed of polyethylene.

At block 52, a solution of 1% to 50% hydrogen peroxide is applied to the interior surfaces and the exterior surfaces of the container. The hydrogen peroxide solution is preferably applied at a temperature ranging from 35° C. to 100° C., more preferably at a temperature ranging from 35° C. to 85° C., even more preferably at a temperature ranging from 50° C. to 75° C., and most preferably at a temperature of 65° C. The solution of hydrogen peroxide preferably has a concentration ranging from 1% to 50% hydrogen peroxide, more preferably 30% to 40%, and most preferably 35%. The hydrogen peroxide is preferably applied to the container in a liquid form. Alternatively, the hydrogen peroxide is applied as a vapor and allowed to condense on the surfaces of the container. Although there is no upper limit, the solution of hydrogen peroxide is preferably allowed to remain on the surfaces of the container for an activation time period of 30 seconds, more preferably less than 30 seconds, even more preferably less than 10 seconds, and most preferably one second or less.

After the activation time period, a solution of ferrous sulfate is applied to the surfaces of the container as set forth in block 53. A one Normal solution of ferrous sulfate is utilized as the solution. The solution of ferrous sulfate is preferably applied at a temperature ranging from 35° C. to 100° C., more preferably at a temperature ranging from 35° C. to 85° C., even more preferably at a temperature ranging from 40° C. to 60° C., and most preferably at a temperature of 50° C. The ferrous sulfate solution reacts with the hydrogen peroxide to generate hydroxyl radicals which kill the microorganisms on the surfaces of the container. The ferrous sulfate solution lessens the sterilization time to achieve aseptic conditions. Further, the ferrous sulfate solution decreases the absorption of hydrogen peroxide by the container and also hydrogen peroxide residue. Yet further, the ferrous sulfate solution allows the sterilization process to be performed at lower temperatures than the prior art sterilization methods, which allows for the use of thinner wall containers.

At block 54, the interior surfaces and exterior surfaces of the container are rinsed to remove hydrogen peroxide residue and also any ferrous sulfate solution. Preferably, the surfaces of the container are rinsed with sterile water. Subsequent to the rinsing, the containers are filled with a product.

Figure 5:
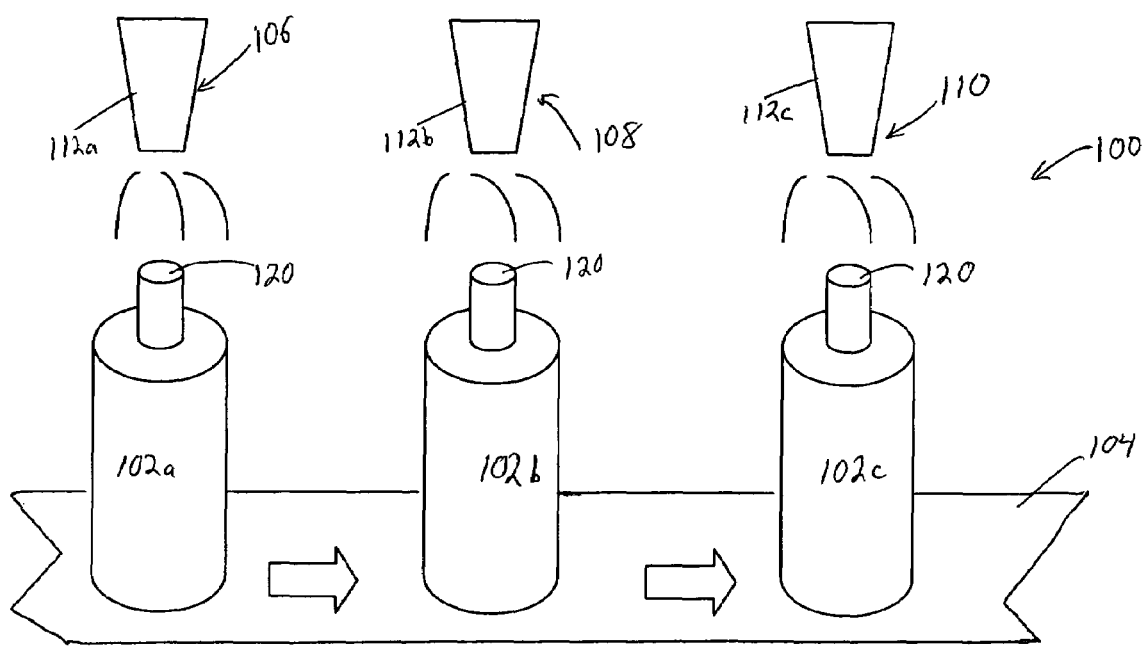
FIG. 5 is a schematic view of containers being sterilized on an apparatus of the present invention.

As shown in FIG. 5, an apparatus for sterilizing containers is generally designated 100. Each of a plurality of containers 102a-c is preferably transported on a conveyor means 104 form various stations. In a preferred embodiment, at a first station 106 hydrogen peroxide is applied to the interior surfaces and exterior surfaces of the container 102a. At a second station 108, the alkaline solution is applied to the interior surfaces and exterior surfaces of the container 102b. At a third station 110, the interior surfaces and exterior surfaces of the container 102c are rinsed, preferably with sterile water. The conveyor means 104 is preferably a conveyor belt that moves according to the activation period necessary for the hydrogen peroxide.

Alternatively, the containers 102 are conveyed upside down to allow gravity to assist in draining the solutions and rinse from the containers subsequent to sterilization.

Yet further in an alternative embodiment, each container 102 is placed at a station and dispensers containing or in flow communication with the various solutions and rinses are moved over or under the containers to dispense each solution or rinse onto the container.

The following examples illustrate the efficacy of the method of the present invention. The experiments were designed to identify the conditions optimal for polymer sterilization and also explore the boundary areas to determine the conditions limiting the efficacy of the treatment. Polymer materials were inoculated with $10^6$ spores of *B. subtilis* var. *globigii* (ATCC 9372) as set forth in the tables. Each polymer strip was inoculated by drop spotting approximately 100 micro-liters and coating the surface by swabbing the surface of the polyethylene strip. The culture was allowed to dry before sterilization. Each strip of polyethylene was treated by vigorously agitating the strip in the appropriate treatment solutions. Each treated polymer strip was then treated with catalase to inactivate residual peroxide, swabbed and plated using TGE incubated at 35° C. for two days.

In Table One, a NaOH control an inoculated untreated control, and two methods of the present invention were measured and the results set forth in Table 1. Five replicate polymer strips were used for each of the two methods of the present invention. A log measurement value is provided below each of the non-log values. The first method uses hydrogen peroxide first and then an alkaline solution of sodium hydroxide. The second method uses an alkaline solution of sodium hydroxide first and then hydrogen peroxide. The sterilization was conducted at 50° C.

TABLE ONE

| Replicate | 1M NaOH Control | Inoculated Untreated Control | 35% $H_2O_2$ + 1M NaOH | 1M NaOH + 35% $H_2O_2$ |
|---|---|---|---|---|
| 1 CFU/Swab | 5,700 | 1,800,000 | <10 | <10 |
| 1 logCFU/Swab | 3.76 | 6.26 | <1.00 | <1.00 |
| 2 CFU/Swab | 210 | 2,700,000 | <10 | <10 |
| 2 logCFU/Swab | 2.32 | 6.43 | <1.0 | <1.0 |
| 3 CFU/Swab | NA | 1,600,000 | <10 | <10 |
| 3 logCFU/Swab | NA | 6.20 | <1.00 | <1.00 |
| 4 CFU/Swab | NA | NA | <10 | <10 |
| 4 logCFU/Swab | NA | NA | <1.00 | <1.00 |
| 5 CFU/Swab | NA | NA | <10 | <10 |
| 5 logCFU/Swab | NA | NA | <1.00 | <1.00 |

As shown in Table One, the methods of the present invention (the two far right columns) killed the microorganisms. The untreated control had 1,800,000 colony forming units ("CFU") while the methods of the present invention successfully sterilized the polymer strips to obtain a value of <10 CFU. Further, the log reduction of CFU was essentially from log 6.26 to <1.0.

TABLE TWO

| Replicate | Inoculated Untreated Control | 50° C. 10 s 0.25M NaOH Control | 50° C. 30 s 35% $H_2O_2$ 10 s catalase | 50° C. 30 s 35% $H_2O_2$ + 10 s 0.25M NaOH | 50° C. 30 s 3.5% $H_2O_2$ 10 s catalase | 50° C. 30 s 3.5% $H_2O_2$ + 10 s 0.25M NaOH | 50° C. 10 s 0.25M NaOH + 10 s 35% $H_2O_2$ + 10 s catalase |
|---|---|---|---|---|---|---|---|
| 1 CFU/Swab | 3,200,000 | 6,300,000 | 40 | 30 | 1,600,000 | 3,700,000 | 1,500 |
| 1 logCFU/Swab | 6.51 | 6.80 | 1.60 | 1.48 | 6.20 | 6.57 | 3.18 |
| 2 CFU/Swab | 4,900,000 | 3,800,000 | 570 | 20 | 4,200,000 | 4,200,000 | 7,900 |
| 2 logCFU/Swab | 6.69 | 6.58 | 2.76 | 1.30 | 6.62 | 6.62 | 3.90 |

TABLE TWO-continued

| Replicate | Inoculated Untreated Control | 50° C. 10 s 0.25M NaOH Control | 50° C. 30 s 35% H$_2$O$_2$ + 10 s catalase | 50° C. 30 s 35% H$_2$O$_2$ + 10 s 0.25M NaOH | 50° C. 30 s 3.5% H$_2$O$_2$ + 10 s catalase | 50° C. 30 s 3.5% H$_2$O$_2$ + 10 s 0.25M NaOH | 50° C. 10 s 0.25M NaOH + 10 s 35% H$_2$O$_2$ + 10 s catalase |
|---|---|---|---|---|---|---|---|
| 3 CFU/Swab | 7,200,000 | 7,900,000 | 20 | 20 | 4,000,000 | 4,200,000 | 7,900 |
| 3 logCFU/Swab | 6.86 | 6.90 | 1.30 | 1.30 | 6.60 | 6.59 | 4.23 |
| 4 CFU/Swab | 3,800,000 | 5,400,000 | 270 | 10 | 3,000,000 | 6,100,000 | 20,000 |
| 4 logCFU/Swab | 6.58 | 6.73 | 2.43 | 1.00 | 6.48 | 6.79 | 4.30 |
| 5 CFU/Swab | NA | NA | 2700 | <10 | 5,000,000 | 2,700,000 | 200,000 |
| 5 logCFU/Swab | NA | NA | 3.43 | <1.00 | 6.70 | 6.43 | 5.30 |
| Std Dev. | 0.15 | 0.13 | 0.86 | 0.21 | 0.19 | 0.13 | 0.77 |
| Average | 6.66 | 6.75 | 2.30 | 1.22 | 6.52 | 6.60 | 4.18 |
| Log reduction | | | 4.35 | 5.44 | 0.14 | 0.06 | 2.48 |

In Table Two, results are presented for a test where the bacteria were spotted, spread on a Petri dish and allowed to dry prior to treatment. The harshness of the sterilization conditions were decreased from the previous run by reducing the concentration of the alkali treatment and by using stagnant, unagitated solutions The results for the inoculated untreated control are set forth in column two, results for a 0.25M NaOH control are set forth in column three, results for a solution having 35% H$_2$O$_2$ applied and an activation time period of 30 seconds followed by a catalase having an activation period of 10 seconds are set forth in column four, results for a solution having 35% H$_2$O$_2$ applied and an activation time period of 30 seconds followed by a solution of 0.25M NaOH having an activation period of 10 seconds are set forth in column five, results for a solution having 3.5% H$_2$O$_2$ applied and an activation time period of 30 seconds followed by a catalase having an activation period of 10 seconds are set forth in column six, results for a solution having 3.5% H$_2$O$_2$ applied and an activation time period of 30 seconds followed by application of a solution of 0.25M NaOH having an activation period of 10 seconds are set forth in column seven, and the results for a application of a solution of 0.25M NaOH having an activation period of 10 seconds, then application of a solution having 35% H$_2$O$_2$ and an activation time period of 10 seconds followed by a catalase having an activation period of 10 seconds are set forth in column eight. A log measurement value is provided below each of the non-log values. The sterilization was conducted at 50° C. The results in Table 2 clearly define the synergy of the combined treatment. Column 2 is the inoculated, untreated control having 10^6.66 bacteria per plate. Column 3 represents the survival for treatment with 0.25% sodium hydroxide and clearly shows no bacteriocidal effect. A thirty second hydrogen peroxide treatment (column 4) results in a 4.35 log inactivation (1.45 log per 10 seconds of treatment) while combining peroxide with sodium hydroxide (column 5) results in one log greater inactivation of bacteria. Hydrogen peroxide at 3.5% concentration alone (column 6) and in combination with 0.25% sodium hydroxide (column 7) had no effect under these conditions. Pretreatment of the spores with 0.25 M sodium hydroxide in combination with a short 10 second treatment with 35% hydrogen peroxide inactivated 2.48 logs of bacteria. This rate of kill per unit time was significantly increased from the treatment with hydrogen peroxide alone (1.45 logs per 10 seconds). Both treatments using the combination of hydrogen peroxide/sodium hydroxide resulted in an order of magnitude increase in the microbial inactivation. The sterilization method of column five had the best results.

In Table Three, a solution of 0.1 Normal potassium hydroxide (KOH) was utilized with a solution of 3% hydrogen peroxide at a temperature of 35° C. for 30 seconds. The results indicate that the treatment was not efficacious under these conditions of treatment.

TABLE THREE

| Replicate | Catalase Control | H$_2$O$_2$ Control | Inoculated Untreated Control | 3% H$_2$O$_2$ + 0.1N KOH | 0.1N KOH + 3% H$_2$O$_2$ |
|---|---|---|---|---|---|
| 1 CFU/Swab | 2,500,000 | 5,200,000 | 2,000,000 | 8,000,000 | 2,500,000 |
| 1 logCFU/Swab | 6.40 | 6.72 | 6.30 | 6.90 | 6.40 |
| 2 CFU/Swab | NA | NA | NA | 8,900,000 | 3,100,000 |
| 2 logCFU/Swab | NA | NA | NA | 6.95 | 6.49 |
| 3 CFU/Swab | NA | NA | NA | 3,700,000 | 2,800,000 |
| 3 logCFU/Swab | NA | NA | NA | 6.57 | 6.45 |
| 4 CFU/Swab | NA | NA | NA | 3,900,000 | 4,100,000 |
| 4 logCFU/Swab | NA | NA | NA | 6.59 | 6.61 |
| 5 CFU/Swab | NA | NA | NA | 7,100,000 | 2,800,000 |
| 5 logCFU/Swab | NA | NA | NA | 6.85 | 6.45 |

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

I claim as my invention:

1. A method for sterilizing packaging, the method comprising:

applying a hydrogen peroxide solution having from 1% to 50% hydrogen peroxide to packaging, the hydrogen peroxide solution applied at a temperature ranging from 35° C. to 100° C.;

permitting the hydrogen peroxide solution to activate on the packaging for an activation period;

applying an alkaline solution to the packaging subsequent to the activation period, the alkaline solution having a pH in the range of 10-14, the alkaline solution applied at a temperature ranging from 35° C. to 100° C.; and rinsing the packaging with sterile water to remove the residue alkaline solution and residue hydrogen peroxide.

2. The method according to claim 1 wherein the alkaline solution is a sodium hydroxide solution.

3. The method according to claim 1 wherein the alkaline solution is a solution of 0.05 Normal sodium hydroxide having a pH of approximately 12.5.

4. The method according to claim 1 wherein the hydrogen peroxide solution has a concentration of approximately 35% hydrogen peroxide.

5. The method according to claim 1 wherein the packaging is a PET bottle, a polyethylene bottle or a polypropylene bottle.

6. The method according to claim 1 wherein the solution of hydrogen peroxide is first applied to the packaging and the activation period is 30 seconds and then the alkaline solution is applied to the packaging to reaction with the hydrogen peroxide to generate hydroxyl radicals.

7. A method for sterilizing a plastic bottle, the method comprising:

applying a hydrogen peroxide solution having from 30% to 40% hydrogen peroxide to an exterior surface of the plastic bottle and an interior surface of the plastic bottle, the hydrogen peroxide solution applied at a temperature ranging from 40° C. to 60° C.;

permitting the hydrogen peroxide solution to activate on the exterior surface of the plastic bottle and the interior surface of the plastic bottle for an activation period;

applying a solution of 0.05 Normal sodium hydroxide to the exterior surface of the plastic bottle and the interior surface of the plastic bottle subsequent to the activation period, the solution of 0.05 Normal sodium hydroxide having a pH in the range of 11-13, the solution of 0.05 Normal sodium hydroxide applied at a temperature ranging from 50° C. to 75° C.; and rinsing the packaging with sterile water to remove the residue sodium hydroxide and residue hydrogen peroxide.

8. The method according to claim 7 wherein the plastic bottle is a PET bottle, a polyethylene bottle or a polypropylene bottle.

9. The method according to claim 7 wherein the solution of hydrogen peroxide is applied as a vapor.

10. A method for sterilizing packaging at a low temperature, the method comprising:

applying a hydrogen peroxide solution having from 1% to 50% hydrogen peroxide to packaging, the hydrogen peroxide solution applied at a temperature no greater than 65° C.;

permitting the hydrogen peroxide solution to activate on the packaging for an activation period ranging from 1 second to 30 seconds;

applying an alkaline solution to the packaging subsequent to the activation period, the alkaline solution having a pH in the range of 10-14, the alkaline solution applied at a temperature no greater than 65° C.; and rinsing the packaging with sterile water to remove the residue alkaline solution and residue hydrogen peroxide.

11. The method according to claim 10 wherein the alkaline solution is a solution of 0.05 Normal sodium hydroxide having a pH of approximately 12.5.

12. The method according to claim 10 wherein the hydrogen peroxide solution has a concentration of approximately 35% hydrogen peroxide.

13. The method according to claim 10 wherein the packaging is a PET bottle, a polyethylene bottle or a polypropylene bottle.

14. The method according to claim 10 wherein the solution of hydrogen peroxide is first applied to the packaging and the activation period is 30 seconds and then the alkaline solution is applied to the packaging to reaction with the hydrogen peroxide to generate hydroxyl radicals.

15. The method according to claim 10 further comprising filling the sterilized packaging with a food product.

16. The method according to claim 15 wherein the food product is a high acid food product.

* * * * *